(12) United States Patent
Hiyoshi et al.

(10) Patent No.: US 6,504,046 B1
(45) Date of Patent: Jan. 7, 2003

(54) PROCESS FOR THE PREPARATION OF AMIDES

(75) Inventors: Hidetaka Hiyoshi; Shuji Taniguchi; Junko Suzuki, all of Shizuoka (JP)

(73) Assignee: Ihara Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 09/720,617

(22) PCT Filed: Apr. 27, 2000

(86) PCT No.: PCT/JP00/02773

§ 371 (c)(1),
(2), (4) Date: Dec. 27, 2000

(87) PCT Pub. No.: WO00/66541

PCT Pub. Date: Nov. 9, 2000

(30) Foreign Application Priority Data

Apr. 28, 1999 (JP) ............................................ 11-122931
Jul. 12, 1999 (JP) ............................................ 11-197529

(51) Int. Cl.$^7$ ........................ C07C 69/00; C07C 229/00
(52) U.S. Cl. ........................ 560/129; 560/155; 564/123
(58) Field of Search ................................ 560/155, 129; 564/123

(56) References Cited

U.S. PATENT DOCUMENTS 5,322,964 A  6/1994  Drewes et al. ............... 564/343
5,659,046 A * 8/1997  Kaweswaran

FOREIGN PATENT DOCUMENTS

EP  0 662 475 B1  11/1994
EP  0 816 330 A1  6/1997

OTHER PUBLICATIONS

Fuganti et al, Tetrahedron Letters, v. 27, 1986, pp. 2295–2298.*
Dow et al, Journal of Organic Chemistry, v. 55, 1990, pp. 386–388.*
Doi et al, Journal of Organic Chemistry, v. 63, 1998, pp. 428–429.*
Doi T, "One–Pot Sequential Asymmetric Hydrogenation Utilizing Rh (I) and Ru (II) Catalysts", J. Org. Chem., 1998, vol. 63, No. 3, pp. 428–429.
Dow R. L., "An Efficient Synthesis of Ethyl 5–Oxazoleacetates", J. Org. Chem., 1990, vol. 55, No. 1, pp. 386–388.
Sauve G. et al., "Carboxyl–modified Amino Acids and Peptides: I) An Efficient Method for the Synthesis of Monofunctionalized Enamines and Monofunctionalized Methyl Ketone Derivatives from Thioamindes via Episulfides and Thioiminium Salts", Tetrahedron Letters, 1988, vol. 29, No. 19, pp. 2295–2298.
Fuganti C. et al., "Further Information on the Steric Course of the Baker's Yeast Reduction of 4–Substituted–3–Oxobutanoates", Tetrahedron Letters, 1986, vol. 27, No. 43, pp. 5275–5276.

* cited by examiner

Primary Examiner—Alan L. Rotman
Assistant Examiner—Héctor M Reyes
(74) Attorney, Agent, or Firm—Kubovcik & Kubovcik

(57) ABSTRACT

A process for producing an amide compound of the following formula

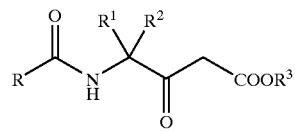

by reacting a nitrile compound of the formula

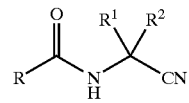

with an acid to obtain an oxazolinone compound of the formula

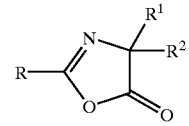

and reacting the oxazolinone compound with a carboxy compound of the formula

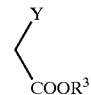

in the presence of a base.

7 Claims, No Drawings

PROCESS FOR THE PREPARATION OF AMIDES

TECHNICAL FIELD

The present invention relates to an amide compound which is a useful intermediate in production of a phenylalkanoic acid amide useful as a fungicide; a process for production thereof; a process for production of an oxazolinone compound which is a raw material used in production of said amide compound; and a process for production of a ketone compound which is also a useful intermediate in production of a phenylalkanoic acid amide from said amide compound.

BACKGROUND ART

Some of the phenylalkanoic acid amides are known to be useful as an effective fungicide (for example, JP-A-9-48750); however, no process is known for producing such a phenylalkanoic acid amide compound from an oxazolinone compound.

As the process for producing an oxazolinone compound, a process is generally known which comprises subjecting an amino acid whose amino group is protected with acyl group, to dehydrative cyclization (Protective Groups in Organic Synthesis, p. 223, 1981, John Wiley & Sons). Besides, a process is also known which comprises producing an oxazolinone from an acylated aminonitrile using oxalyl chloride or chlorooxoacetate (Tetrahedron, Vol. 40, pp. 2395 to 2404, 1984). These processes, however, have drawbacks in that it is difficult to obtain a corresponding amino acid or impossible to produce an intended oxazolinone compound at a low cost industrially.

The present invention aims at providing important intermediates used in production of a phenylalkanoic acid amide compound showing an excellent fungicidal effect; and novel and simple processes for producing such an intermediate or a raw material compound used in production of the intermediate.

DISCLOSURE OF THE INVENTION

The present inventor made a hard study zealously in order to solve the above subject. As a result, the present inventor surprisingly found out that an amide compound which is an important intermediate for phenylalkanoic acid amide compound can be easily formed by reacting an oxazolinone compound with a carboxy compound (e.g. malonic acid half ester) in the presence of a base. The present inventor also found out that the above oxazolinone compound can be obtained by a simple process of reacting a nitrile compound of high availability with an acid. The present invention has been completed based on the above findings.

BEST MODE FOR CARRYING OUT THE INVENTION

The present invention is described in detail below.

The present invention provides the inventions described in the following [1] to [6].

[1] A process for producing an amide compound represented by the following general formula

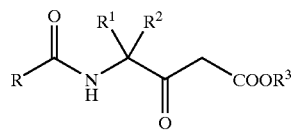

[wherein R is an alkyl group, a cycloalkyl group, a haloalkyl group, an aryl group, a substituted aryl group, an arylalkyl group, a substituted arylalkyl group, an (aryl)(alkoxy)alkyl group or a (substituted aryl)(alkoxy)alkyl group; $R^1$ and $R^2$ where each independently an alkyl group, a cycloalkyl group, a haloalkyl group, an arylalkyl group, a substituted arylalkyl group, an aryl group, a substituted aryl group or a hydrogen atom, and may bond with each other to form a ring together with the carbon atom with which they bond; and $R^3$ is an alkyl group, a cycloalkyl group, a haloalkyl group, an arylalkyl group, a substituted arylalkyl group, an aryl group, a substituted aryl group or a hydrogen atom], which process comprises reacting a nitrile compound represented by the following general formula

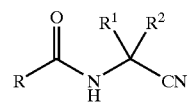

(wherein R, $R^1$ and $R^2$ each have the same definition as given above) with an acid to give rise to intramolecular ring closure to obtain an oxazolinone compound represented by the following general formula

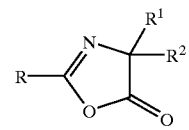

(wherein R, $R^1$ and $R^2$ each have the same definition as given above), and reacting the oxazolinone compound with a carboxy compound represented by the following general formula

(wherein Y is a hydrogen atom, a carboxyl group or a salt of the carboxyl group; and $R^3$ has the same-definition as given above) in the presence of a base.

[2] A process for producing an oxazolinone compound represented by the following general formula

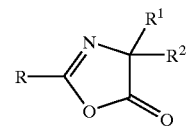

[wherein R is an alkyl group, a cycloalkyl group, a haloalkyl group, an aryl group, a substituted aryl group, an arylalkyl group, a substituted arylalkyl group, an (aryl)(alkoxy)alkyl group or a (substituted aryl)(alkoxy)alkyl group; and $R^1$ and $R^2$ are each independently an alkyl group, a cycloalkyl group, a haloalkyl group, an arylalkyl group, a substituted arylalkyl group, an aryl group, a substituted aryl group or a hydrogen atom, and may bond with each other to form a ring together with the carbon atom with which they bond], which process comprises reacting a nitrile compound represented by the following general formula

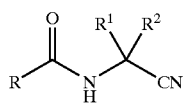

(wherein R, $R^1$ and $R^2$ each have the same definition as given above) with an acid to give rise to intramolecular ring closure.

[3] A process for producing an amide compound represented by the following general formula

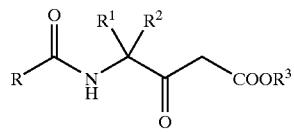

[wherein R is an alkyl group, a cycloalkyl group, a haloalkyl group, an aryl group, a substituted aryl group, an arylalkyl group, a substituted arylalkyl group, an (aryl)(alkoxy)alkyl group or a (substituted aryl)(alkoxy)alkyl group; $R^1$ and $R^2$ are each independently an alkyl group, a cycloalkyl group, a haloalkyl group, an arylalkyl group, a substituted arylalkyl group, an aryl group, a substituted aryl group or a hydrogen atom, and may bond with each other to form a ring together with the carbon atom with which they bond; and $R^3$ is an alkyl group, a cycloalkyl group, a haloalkyl group, an arylalkyl group, a substituted arylalkyl group, an aryl group, a substituted aryl group or a hydrogen atom], which process comprises reacting an oxazolinone compound represented by the following general formula

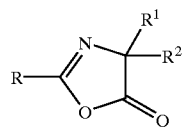

(wherein R, $R^1$ and $R^2$ each have the same definition as given above) with a carboxy compound represented by the following general formula

(wherein Y is a hydrogen atom, a carboxyl group or a salt of the carboxyl group; and $R^3$ has the same definition as given above) in the presence of a base.

[4] A process for producing a ketone compound represented by the following general formula

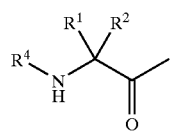

[wherein $R^1$ and $R^2$ are each independently an alkyl group, a cycloalkyl group, a haloalkyl group, an arylalkyl group, a substituted arylalkyl group, an aryl group, a substituted aryl group or a hydrogen atom, and may bond with each other to form a ring together with the carbon atom with which they bond; and $R^4$ is an alkylcarbonyl group, a cycloalkylcarbonyl group, a haloalkylcarbonyl group, an arylcarbonyl group, a substituted arylcarbonyl group, an arylalkylcarbonyl group, a substituted arylalkylcarbonyl group, an (aryl)(alkoxy)alkylcarbonyl group, a (substituted aryl)(alkoxy)alkylcarbonyl group or a hydrogen atom], which process comprises reacting an amide compound represented by the following general formula

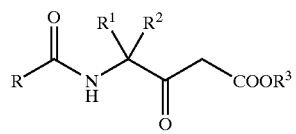

[wherein R is an alkyl group, a cycloalkyl group, a haloalkyl group, an aryl group, a substituted aryl group, an arylalkyl group, a substituted arylalkyl group, an (aryl)(alkoxy)alkyl group or a (substituted aryl)(alkoxy)alkyl group; $R^1$ and $R^2$ each have the same definition as given above; and $R^3$ is an alkyl group, a cycloalkyl group, a haloalkyl group, an arylalkyl group, a substituted arylalkyl group, an aryl group, a substituted aryl group or a hydrogen atom] with an acid or a base in the presence of water.

[5] A process for producing an amide compound, set forth in the above [1] or [3], wherein the base is selected from alkali metal bases, alkaline earth metal bases, organic amines and pyridines.

[6] An acid amide compound represented by the following general formula

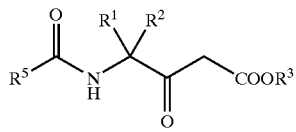

[wherein $R^5$ is an alkyl group, a cycloalkyl group, a haloalkyl group, an arylalkyl group, a substituted arylalkyl group, an (aryl)(alkoxy)alkyl group or a (substituted aryl)(alkoxy)-alkyl group; and $R^1$ and $R^2$ are each independently an alkyl group, a cycloalkyl group, a haloalkyl group, an arylalkyl group, a substituted arylalkyl group, an aryl group, a substituted aryl group or a hydrogen atom, and may bond with each other to form a ring together with the carbon atom with which they bond; $R^3$ is an alkyl group, a cycloalkyl group, a haloalkyl group, an arylalkyl group, a substituted arylalkyl group, an aryl group, a substituted aryl group or a hydrogen atom].

First, the invention of the above [1] is described.

In the invention of [1], first, a nitrile compound represented by the following general formula

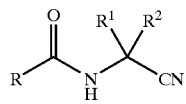

is reacted with an acid to give rise to intramolecular ring closure to obtain an oxazolinone compound represented by the following general formula

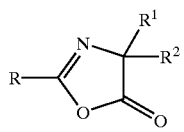

(this process corresponds to the invention described in the above [2]).

The nitrile compound used as a raw material in this process of the present invention may be any compound which is represented by the above general formula. In the general formula, R is a straight chain or branched chain alkyl group having 1 to 6 carbon atoms (hereinafter, carbon atoms, for example, 1 to 6 carbon atoms are referred to as "C1 to C6"), such as methyl group, ethyl group, n-propyl group, isopropyl group, n-butyl group, sec-butyl group, tert-butyl group, n-pentyl group, n-hexyl group or the like; a straight chain or branched chain C1 to C6 haloalkyl group such as trifluoromethyl group, chloromethyl group, dichloromethyl group, trichloromethyl group or the like; a C3 to C6 cycloalkyl group such as cyclopropyl group, cyclobutyl group, cyclopentyl group, cyclohexyl group or the like; an aryl group such as phenyl group, naphthyl group or the like; a halogen-, C1 to C6 alkyl- or C1 to C6 alkoxy-substituted aryl group such as 2-chlorophenyl group, 4-chlorophenyl group, 4-methylphenyl group, 4-methoxyphenyl group or the like; an aryl(C1 to C6)alkyl group such as phenylmethyl group, 1-phenylethyl group or the like; a halogen-, C1 to C6 alkyl- or C1 to C6 alkoxy-substituted aryl(C1 to C6)alkyl group such as 1-(4-chlorophenyl)ethyl group, 1-(4-methylphenyl)ethyl group, 1-(4-methoxyphenyl)ethyl group or the like; an (aryl) (C1 to C6 alkoxy) (C1 to C6)alkyl group wherein an alkyl group is substituted with an aryl group (e.g. phenyl group or naphthyl group) and a C1 to C6 alkoxy group (e.g. methoxy group, ethoxy group, n-propoxy group, isopropoxy group, n-butoxy group, isobutoxy group, n-pentyloxy group or n-hexyloxy group), such as 1-phenyl-1-methoxymethyl group or the like; or a (substituted aryl) (C1 to C6 alkoxy)(C1 to C6)alkyl group wherein an alkyl group is substituted with a halogen-, C1 to C6 alkyl- or C1 to C6 alkoxy-substituted aryl group (e.g. 2-chlorophenyl group, 4-chlorophenyl group, 2-fluorophenyl group, 4-fluorophenyl group, 4-methoxyphenyl group, 4-methylphenyl group or 2-methylphenyl) and a C1 to C6 alkoxy group (e.g. methoxy group, ethoxy group, n-propoxy group, isopropoxy group, n-butoxy group, isobutoxy group, n-pentyloxy group or n-hexyloxy group), such as 1-(4-chlorophenyl)-1-methoxymethyl group or the like.

$R^1$ and $R^2$ are each independently a straight chain or branched chain C1 to C6 alkyl group such as methyl group, ethyl group, n-propyl group, isopropyl group, n-butyl group, sec-butyl group, tert-butyl group, n-pentyl group, n-hexyl group or the like; a straight chain or branched chain C1 to C6 haloalkyl group such as trifluoromethyl group, chloromethyl group, dichloromethyl group, trichloromethyl group or the like; a C3 to C6 cycloalkyl group such as cyclopropyl group, cyclobutyl group, cyclopentyl group, cyclohexyl group or the like; an aryl(C1 to C6)alkyl group such as phenyl methyl group, 1-phenylethyl group or the like; a halogen-, C1 to C6 alkyl- or C1 to C6 alkoxy-substituted aryl(C1 to C6)alkyl group, such as 1-(4-chlorophenyl)ethyl group, 1-(2-chlorophenyl)ethyl group, 1-(4-methylphenyl) ethyl group, 1-(4-methoxyphenyl)ethyl group or the like; an aryl group such as phenyl group, naphtyl group or the like; a halogen-, C1 to C6 alkyl- or C1 to C6 alkoxy-substituted aryl group such as 2-chlorophenyl group, 4-chlorophenyl group, 4-methylphenyl group, 4-methoxy phenyl group or the like; or a hydrogen atom. $R^1$ and $R^2$ may bond with each other to form a C3 to C6 ring together with the carbon atom with which they bond.

As specific examples of the nitrile compound having such substituents, represented by the above general formula, there can be mentioned N-(1-cyano-1-methyl-propyl)acetamide, N-(1-cyano-1,2-dimethylpropyl)acetamide, N-(1-cyano-1,2-dimethylpropyl)benzamide, 4-chloro-N-(1-cyano-1,2-dimethylpropyl)benzamide, 4-methyl-N-(1-cyano-1,2-dimethylpropyl)benzamide, 2-(4-chlorophenyl)-N-(1-cyano-1,2-dimethylpropyl)propanamide, N-(1-cyano-1,2-dimethylpropyl)-2,2,2-trifluoroacetamide, N-(1-cyano-1,2-dimethylpropyl)cyclopropanamide, N-(1-cyano-1,2-dimethylpropyl)benzamide, N-(1-cyano-1,2-dimethylpropyl)-4-chlorobenzamide, N-(1-cyano-1,2-dimethylpropyl)-4-methoxybenzamide, N-(1-cyano-1,2-dimethylpropyl)phenylacetamide, 2-(4-chlorophenyl)-N-(1-cyano-1,2-dimethylpropyl)acetamide, 2-(4-methoxyphenyl)-N-(1-cyano-1,2-dimethylpropyl) acetamide, N-(1-cyano-1-trifluoromethyl-2-methylpropyl) acetamide, N-(1-cyano-1-phenylpropyl)acetamide, N-[1-cyano-1-(4-chlorophenyl)propyl]acetamide, N-[1-cyano-1-(4-methoxyphenyl)propyl]acetamide, N-(1-cyano-1-benzylpropyl)acetamide, N-[1-{(4-chlorophenyl)methyl}-1-cyano-propyl]acetamide, N-[1-{(4-methoxyphenyl)methyl}-1-cyano-propyl]acetamide, N-(1-cyano-1-cyclopropylethyl)acetamide and 2-(4-chlorphenyl)-N-(1-cyano-1,2-dimethylpropyl)-2-methoxy-acetamide.

Some of the nitrile compounds represented by the above general formula are publicly known compounds, otherwise, can be produced by using, for example, a corresponding acid halide and aminonitrile according to, for example, a process described in Organic Synthesis Collective Volume, V, p. 336 (1973).

As the acid used in the present invention process (intramolecular ring closure reaction), there can be mentioned, for example, mineral acids such as hydrochloric acid, sulfuric acid and the like; carboxylic acids such as formic acid, acetic acid and the like; and acidic ion exchange resins such as Amberlist and the like. A combination of two or more kinds of acids may be used, but sulfuric acid is used preferably. The amount of the acid used can be in such a range that the oxazolinone compound formed is not decomposed; however, it is, for example, 0.1 to 2 moles, preferably 0.5 to 1 mole per 1 mole of the nitrile compound represented by the above general formula.

The reaction is conducted ordinarily using a solvent. As the solvent usable, there can be mentioned, for example, acetic acid esters such as methyl acetate, ethyl acetate, propyl acetate and the like; nitriles such as acetonitrile and the like; ethers such as tetrahydrofuran, dioxane, diethyl ether and the like; aromatic hydrocarbons such as toluene, xylene, chlorobenzene and the like; aliphatic hydrocarbons such as hexane, cyclohexane and the like; aprotic polar solvents such as dimethylformamide, dimethylacetamide and the like; halogenated aliphatic hydrocarbons such as chloroform, dichloromethane and the like; ethylene glycols such as polyethylene glycol 400 (PEG 400) and the like; and aliphatic carboxylic acids such as glacial acetic acid and the like. These solvents can be used singly or as a mixed solvent consisting of any proportions of two or more kinds of solvents. The amount of the solvent used can be such a level to allow sufficient stirring; and it can be, for example, 0.5 to 3 liters, preferably 1 to 3 liters per 1 mole of the nitrile compound represented by the above general formula.

In the reaction, when water is present in the reaction system in an amount of 0.0005 to 1 mole, preferably 0.1 to 1 mole per 1 mole of the nitrile compound represented by the above general formula, the yield of the intended product is high in some cases.

The temperature of the reaction can be selected in a range from −20° C. to the refluxing temperature of the solvent used; however, it is preferably 0 to 80° C. As to the time of the reaction, there is no particular restriction; however, it is preferably 0.5 to 12 hours.

As specific examples of the oxazolinone compound represented by the above general formula, obtained as above, there can be mentioned 4-isopropyl-2,4-dimethyl-1,3-oxazol-5-one, 4-isopropyl-4-methyl-2-phenyl-1,3-oxazol-5-one, 2-[1-(4-chlorophenyl)ethyl]-4-isopropyl-4-methyl-1,3-oxazol-5-one, 4-ethyl-4-methyl-2-trifluoromethyl-1,3-oxazol-5-one, 2-cyclohexyl-4-isobutyl-4-methyl-1,3-oxazol-5-one, 4,4-diethyl-2-pentyl-1,3-oxazol-5-one, 2-(2-chlorophenyl)-4-isopropyl-4-methyl-1,3-oxazol-5-one, 4-benzyl-2,4-dimethyl-1,3-oxazol-5-one, 4-(4-chlorobenzyl)-2,4-dimethyl-1,3-oxazol-5-one, 4-(4-methoxybenzyl)-2,4-dimethyl-1,3-oxazol-5-one, 4-(4-methylbenzyl)-2,4-dimethyl-1,3-oxazol-5-one and 2-[1-(4-chlorophenyl)-1-methoxymethyl]-4-isopropyl-4-methyl-1,3-oxazol-5-one.

Some of the oxazolinone compounds are known compounds; or can be produced by the above reaction; besides by using a corresponding amino acid and a carboxylic acid halide as raw materials according to a process described in, for example, Bulletin de la Societe Chimique de France, p. 543 (1958).

In the invention described in the above [1], then, the oxazolinone compound represented by the following general formula

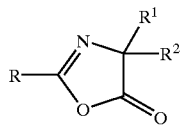

is reacted with a carboxy compound represented by the following general formula

in the presence of a base to produce an amide compound represented by the following general formula

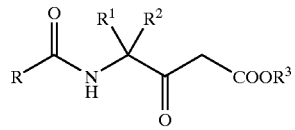

(this reaction corresponds to the invention described in the above [3]).

In the carboxy compound represented by the above general formula, $R^3$ is a straight chain or branched chain C1 to C6 alkyl group such as methyl group, ethyl group, n-propyl group, isopropyl group, n-butyl group, sec-butyl group, tert-butyl group, n-pentyl group, n-hexyl group or the like; a C3 to C6 cycloalkyl group such as cyclopropyl group, cyclobutyl group, cyclopentyl group, cyclohexyl group or the like; a straight chain or branched chain C1 to C6 haloalkyl group such as trifluoromethyl group, chloromethyl group, 2-fluoroethyl group or the like; an aryl group such as phenyl group, naphthyl group or the like; a halogen-, C1 to C6 alkyl- or C1 to C6 alkoxy-substituted aryl group such as 2-chlorophenyl group, 4-chlorophenyl group, 2-fluorophenyl group, 4-fluorophenyl group, 4-methoxyphenyl group, 4-methylphenyl group, 2-methylphenyl group or the like; an aryl(C1 to C6)alkyl group such as phenylmethyl group, 1-phenylethyl group or the like; a halogen-, C1 to C6 alkyl- or C1 to C6 alkoxy-substituted aryl(C1 to C6)alkyl group such as 1-(4-chlorophenyl)ethyl group, 1-(2-chlorophenyl)ethyl group, 1-(4-methylphenyl)ethyl group, 1-(4-methoxyphenyl)ethyl group or the like; or a hydrogen atom. Y is a hydrogen atom, a carboxyl group or a salt of the carboxyl group. The salt can be exemplified by those of an alkali metal (e.g. sodium or potassium), an alkaline earth metal (e.g. calcium or barium), an amine (e.g. triethylamine or diethylamine) and a pyridine (e.g. pyridine).

Therefore, as specific examples of the carboxy compound represented by the above general formula, usable in the present invention process, there can be mentioned methyl acetate, ethyl acetate, propyl acetate, butyl acetate, monopotassium methyl malonate, monopotassium ethyl malonate, monopotassium tert-butyl malonate, ditriethylamine salt of malonic acid, disodium malonate, monosodium ethyl malonate, monopotassium isopropyl malonate and malonic acid.

The carboxy compound represented by the above general formula is a known compound, or can be produced by a known process using, for example, a corresponding malonic acid diester and a base as raw materials according to a process described in, for example, The Journal of Organic Chemistry, p. 2536 (1980).

The reaction between the oxazolinone compound represented by the above general formula and the carboxy compound represented by the above general formula proceeds in any molar ratio of the two compounds. However, the carboxy compound represented by the above general formula is used in an amount of, for example, ordinarily 0.5 to 3 moles, preferably 1 to 2 moles per 1 mole of the oxazolinone compound represented by the above general formula.

The reaction is conducted ordinarily using a solvent. As the solvent usable in the reaction, there can be mentioned, for example, acetic acid esters such as methyl acetate, ethyl acetate, propyl acetate and the like; nitriles such as acetonitrile and the like; ethers such as tetrahydrofuran, dioxane, diethyl ether and the like; aromatic hydrocarbons such as toluene, xylene, chlorobenzene and the like; aprotic polar solvents such as dimethylformamide, dimethylacetamide and the like; halogenated hydrocarbons such as chloroform, dichloromethane and the like; and pyridines such as pyridine and the like. These solvents can be used singly or as a mixed solvent consisting of any proportions of two or more kinds of solvents. The amount of the solvent usable can be such a level as to allow the sufficient mixing of the reaction system; and it can be, for example, 1 to 5 liters, preferably 1 to 3 liters per 1 mole of the oxazolinone compound represented by the above general formula.

The reaction is carried out in the presence of a base. As the base, there can be mentioned, for example, alkali metal bases such as sodium hydride, potassium hydride, potassium carbonate, sodium amide, lithium diisopropylamide (LDA) and the like; alkaline earth metal salts such as magnesium ethoxide and the like; organic amines such as triethylamine, 1,8-diazabicyclo[5.4.0]-7-undecene (DBU) and the like; and pyridines such as dimethylaminopyridine (DMAP) and the like. As to the amount of the base used, there is no particular restriction as long as the amount does not hinder the reaction; however, the amount is, for example, ordinarily 0.1 to 3 moles, preferably 0.1 to 2 moles per 1 mole of the oxazolinone compound represented by the above general formula.

The base can be used in combination with a Lewis acid such as magnesium chloride, zinc chloride, boron trifluoride or the like. As to the amount of the Lewis acid used in combination, there is no particular restriction as long as the amount does not hinder the reaction; however, the amount is 0.1 to 3 moles, preferably 0.1 to 2 moles per 1 mole of the oxazolinone compound represented by the above general formula.

The temperature of the reaction can be, for example, −78° C. to the refluxing temperature of the solvent used, and is preferably 0 to 100° C. As to the time of the reaction, there is no particular restriction, but the time is preferably 1 to 24 hours.

Next, description is made on the invention described in the above [4].

The invention described in [4] comprises reacting an amide compound represented by the following general formula

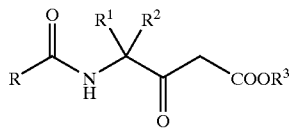

with an acid or a base in the presence of water to give rise to hydrolysis and decarboxylation to produce a ketone compound represented by the following general formula.

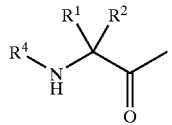

In the amide compound represented by the above general formula and the ketone compound represented by the above general formula, R, $R^1$, $R^2$ and $R^3$ each have the same definition as in the above-described invention of [1].

In the ketone compound represented by the above general formula, $R^4$ is a straight chain or branched chain (C1 to C6 alkyl)carbonyl group such as acetyl group, propionyl group, butyryl group, valeryl group, hexanoyl group, pivaloyl group or the like; a (C3 to C6 cycloalkyl)carbonyl group such as cyclopropylcarbonyl group, cyclobutylcarbonyl group, cyclopentylcarbonyl group, cyclohexylcarbonyl group or the like; a straight chain or branched chain (C1 to C6 haloalkyl)carbonyl group such as trifluoroacetyl group, chloroacetyl group, 3-fluoropropionyl group or the like; an arylcarbonyl group such as benzoyl group or the like; a halogen-, C1 to C6 alkyl- or C1 to C6 alkoxy-substituted arylcarbonyl group such as 2-chlorobenzoyl group, 4-fluorobenzoyl group, 2-methylbenzoyl group, 4-methoxybenzoyl group or the like; an aryl(C1 to C6 alkyl)carbonyl group such as phenylacetyl group or the like; a halogen-, C1 to C6 alkyl- or C1 to C6 alkoxy-substituted aryl(C1 to C6)alkylcarbonyl group such as 2-chlorophenylacetyl group, 4-methylphenylacetyl group, 4-methoxyphenylacetyl group, 1-(4-chlorophenyl)propionyl group or the like; an (aryl) (C1 to C6 alkoxy) (C1 to C6)alkylcarbonyl group wherein an alkyl group is substituted with an aryl group (e.g. phenyl group or naphthyl group) and a C1 to C6 alkoxy group (e.g. methoxy group, ethoxy group, n-propoxy group, isopropoxy group, n-butoxy group, isobutoxy group, n-pentyloxy group or n-hexyloxy group), such as (1-phenyl-1-methoxy)methylcarbonyl group or the like; a (substituted aryl) (C1 to C6 alkoxy) (C1 to C6)alkylcarbonyl group wherein an alkyl group is substituted with a halogen-, C1 to C6 alkyl- or C1 to C6 alkoxy-substituted aryl group (e.g. 2-chlorophenyl group, 4-chlorophenyl group, 2-fluorophenyl group, 4-fluorophenyl group, 4-methoxyphenyl group, 4-methylphenyl group or 2-methylphenyl group) and a C1 to C6 alkoxy group (e.g. methoxy group, ethoxy group, n-propoxy group, isopropoxy group, n-butoxy group, isobutoxy group, n-pentyloxy group or n-hexyloxy group), such as [1-(4-chlorophenyl)-1-methoxy]methylcarbonyl group or the like; or a hydrogen atom.

In this present invention process, the hydrolysis and decarboxylation of the amide compound in the presence of water is conducted using an acid or a base. As the acid usable in the reaction, there can be mentioned, for example, mineral acids such as hydrochloric acid, sulfuric acid and the like; acetic acids such as acetic acid, trifluoroacetic acid and the like; sulfonic acids such as p-toluenesulfonic acid and the like; and acidic ion exchange resins such as Amberlist and the like. As the base usable in the reaction, there can be mentioned, for example, alkali metal hydroxides such as sodium hydroxide, potassium hydroxide and the like; alkali metal carbonates such as sodium carbonate, potassium carbonate and the like; alkaline earth metal hydroxides such as barium hydroxide and the like; organic amines such as 1,8-diazabicyclo[5.4.0]-7-undecene (DBU) and the like; pyridines such as dimethylaminopyridine (DMAP) and the like; and alcholates such as sodium methoxide and the like. The reaction is conducted using preferably a mineral acid, particularly preferably hydrochloric acid or sulfuric acid. In the decomposition reaction, the amount of the acid or base used is not restricted as long as it causes no decomposition of the formed ketone compound represented by the above general formula; however, it is generally 0.001 to 10 moles, preferably 0.1 to 5 moles per 1 mole of the amide compound represented by the above general formula.

The reaction is carried out in the presence of water. The amount of the water used may be 1 mole (18 ml) or more per 1 mole of the amide compound represented by the above general formula, and is, for example, ordinarily 1 to 5,000 moles (90 l), preferably 1 to 1,000 moles. When the reaction is conducted using an acid, the amount of the water is preferably such that the pH of the reaction system becomes about 4 or less although it differs depending upon the kind or amount of the acid used.

The reaction proceeds sufficiently even without using any solvent, but may be conducted using a solvent. The solvent usable in the decomposition reaction may be any solvent which does not hinder the reaction. As the solvent, there can be mentioned, for example, aromatic hydrocarbons such as toluene, xylene, chlorobenzene and the like; acetic acid esters such as methyl acetate, ethyl acetate, butyl acetate and the like; alcohols such as methanol, ethanol, n- propanol, 2-propanol and the like; aprotic polar solvents such as dimethylformamide, dimethylacetamide and the like; ether type solvents such as diethyl ether, tetrahydrofuran, dioxane, monoglyme, diglyme and the like; aliphatic hydrocarbons such as pentane, n-hexane and the like; nitrites such as acetonitrile and the like; ketones such as acetone, methyl ethyl ketone, methyl isobutyl ketone and the like; polyethylene glycols such as polyethylene glycol (PEG) 400 and the like; and water. These solvents can be used singly or as a mixed solvent consisting of any proportions of two or more kinds. The amount of the solvent used can be such a level as to allow the sufficient stirring of the reaction system, but is ordinarily 0.5 to 5 liters, preferably 1 to 3 liters per 1 mole of the amide compound represented by the above general formula.

The temperature of the reaction is, for example, −20° C. to the refluxing temperature of the solvent used, but is preferably 0 to 80° C.

As to the time of the reaction, there is no particular restriction, but the time is preferably 0.5 to 12 hours.

In the reaction, by selecting the reaction conditions appropriately, it is possible to produce even a ketone compound represented by the above general formula wherein $R^1$ is a hydrogen atom or a compound wherein $R^4$ is a substituent other than hydrogen atom; or, it is possible to once produce a compound wherein $R^4$ is a substituent other than hydrogen atom and, after subjecting the compound to isolation and purification as necessary, allow the decomposition to proceed further to produce a compound wherein $R^4$ is a hydrogen atom.

In the reaction, it is thought that first, $R^3$ is hydrolyzed in the reaction system and thereby a compound wherein $R^3$ is a hydrogen atom (or a salt thereof), is formed as an intermediate, and successively this compound (or a salt thereof) quickly gives rise to decarboxylation under the reaction conditions. It is thought that depending upon the reaction conditions employed, even the amide bond is hydrolyzed and the decomposition proceeds so as to produce a compound wherein $R^4$ is a hydrogen atom.

Successively, the invention of [6] is described.

The invention described in the above [6] provides an acid amide compound represented by the above general formula. This acid amide compound can be produced by the process described in the above [1].

In the above general formula, $R^5$ is a straight chain or branched chain C1 to C6 alkyl group, such as methyl group, ethyl group, n-propyl group, isopropyl group, n-butyl group, sec-butyl group, tert-butyl group, n-pentyl group, n-hexyl group or the like; a C3 to C6 cycloalkyl group such as cyclopropyl group, cyclobutyl group, cyclopentyl group, cyclohexyl group or the like; a straight chain or branched chain C1 to C6 haloalkyl group such as trifluoromethyl group, chloromethyl group, 2-fluoroethyl group or the like; an aryl(C1 to C6)alkyl group such as phenylmethyl group, 1-phenylethyl group or the like; a halogen-, C1 to C6 alkyl- or C1 to C6 alkoxy-substituted aryl(C1 to C6)alkyl group such as 1-(4-chlorophenyl)ethyl group, 1-(4-methylphenyl) ethyl group, 1-(4-methoxyphenyl)ethyl group or the like; an (aryl) (C1 to C6 alkoxy) (C1 to C6)alkyl group wherein an alkyl group is substituted with an aryl group (e.g. phenyl group or naphthyl group) and a C1 to C6 alkoxy group (e.g. methoxy group, ethoxy group, n-propoxy group, isopropoxy group, n-butoxy group, isobutoxy group, n-pentyloxy group or n-hexyloxy group), such as 1-phenyl-1-methoxymethyl group or the like; or a (substituted aryl) (C1 to C6 alkoxy) (C1 to C6)alkyl group wherein an alkyl group is substituted with a halogen-, C1 to C6 alkyl- or C1 to C6 alkoxy-substituted aryl group (e.g. 2-chlorophenyl group, 4-chlorophenyl group, 2-fluorophenyl group, 4-fluorophenyl group, 4-methoxyphenyl group, 4-methylphenyl group or 2-methylphenyl) and a C1 to C6 alkoxy group (e.g. methoxy group, ethoxy group, n-propoxy group, isopropoxy group, n-butoxy group, isobutoxy group, n-pentyloxy group or n-hexyloxy group), such as 1-(4-chlorophenyl)-1-methoxymethyl group or the like. $R^1$, $R^2$ and $R^3$ each have the same definition as given in the above [1].

The acid amide compound represented by the above general formula includes those which have one or more asymmetric carbon atom in the molecule and which take an enantiomer or diastereomer form. The present invention compound includes all of such pure isomers and their mixtures (e.g. racemic modifications) of any proportions.

Examples of the present invention compound are shown in Table 1. However, the present invention compound is not restricted thereto and includes all the compounds represented by the above general formula.

Incidentally, the abbreviations In Table 1 refer to the followings.

Me: methyl group
Et: ethyl group
i-Pr: isopropyl group
c-Pr: cyclopropyl group
t-Bu: tert-butyl group
c-Hex: cyclohexyl group
Ph: phenyl group
4-Cl-Ph: 4-chlorophenyl group
Bn: benzyl group
4-Cl-Bn: 4-chlorobenzyl group
1-(4-Cl-Ph)-Et: 1-(4-chlorophenyl)ethyl group
4-Cl-α-CH$_3$O-Bn: 4-chloro-α-(-methoxybenzyl group

TABLE 1

| Compound No. | $R^1$ | $R^2$ | $R^3$ | $R^5$ | Melting point (° C.) |
|---|---|---|---|---|---|
| 1 | Me | Me | Me | Me | |
| 2 | Me | Et | Me | Me | |
| 3 | Et | Et | Me | Me | |
| 4 | Me | i-Pr | Et | Me | 71.0~73.0 |
| 5 | Me | i-Pr | t-Bu | Me | |
| 6 | Me | i-Pr | Et | 1-(4-Cl—Ph)—Et | 92.5~99.7 |
| 7 | Me | i-Pr | Bn | 1-(4-Cl—Ph)—Et | |
| 8 | Me | i-Pr | Me | 1-(4-Cl—Ph)—Et | 104.0~110.0 |
| 9 | Me | i-Pr | t-Bu | 1-(4-Cl—Ph)—Et | |
| 10 | CF$_3$ | Me | Ph | 4-Cl—Bn | |
| 11 | c-Pr | Me | 4-Cl—Ph | CF$_3$ | |
| 12 | Ph | Me | 4-Cl—Bn | c-Hex | |
| 13 | 4-Cl—Ph | Me | c-Hex | Me | |
| 14 | Bn | Me | CH$_2$CF$_3$ | Me | |
| 15 | 4-Cl—Bn | Me | Et | Me | |
| 16 | Me | i-Pr | i-Pr | 1-(4-Cl—Ph)—Et | 110.4~112.8 |
| 17 | Me | i-Pr | Et | 4-Cl—Bn | 96.3~98.3 |
| 18 | Me | i-Pr | Et | 4-Cl-α-CH$_3$O-Bn | |
| 19 | Me | i-Pr | H | 1-(4-Cl—Ph)—Et | 161.8~164.8 |

Below is shown an example of the reaction scheme in which a phenylalkanoic acid amide (which can become a fungicide) is produced from an oxazolinone compound resented by the above general formula via a ketone pound represented by the above general formula.

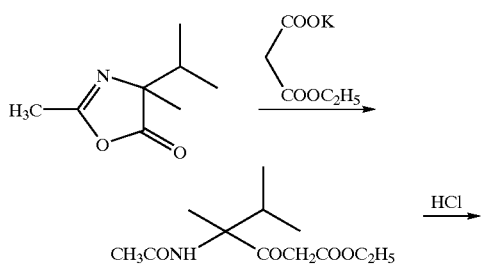

-continued

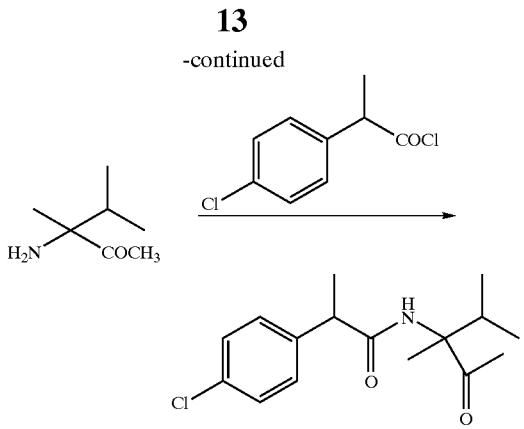

As shown in the above scheme, the present invention processes (described in the above [1] to [5]) and the present invention compound (described in the above [6]) are very useful in production of a phenylalkanoic acid amide which is an active ingredient for fungicide.

Next, the processes for producing the present invention products are described specifically by way of Examples.

EXAMPLE 1
(The Invention Described in the Above [2])

Production of 2-phenyl-4-isopropyl-4-methyl-1,3-oxazol-5-one 40 ml of glacial acetic acid, 3.92 g (0.038 mole) of concentrated sulfuric acid and 0.36 g (0.02 mole) of water were added to 8.6 g (0.04 mole) of N-(1-cyano-1,2-dimethylpropyl)benzamide. The mixture was stirred at 80° C. for 2 hours to give rise to a reaction. After the completion of the reaction, the reaction mixture was cooled. Thereto were added 100 ml of water and 100 ml of ethyl acetate for layer separation. The organic layer was washed with a saturated aqueous sodium bicarbonate solution and a saturated aqueous sodium chloride solution, and concentrated to obtain 7.2 g (0.033 mole) of 2-phenyl-4-isopropyl-4-methyl-1,3-oxazol-5-one (yield=83%).

EXAMPLE 2
(The Invention Described in the Above [2])

Production of 2-[1-(4-chlorophenyl)ethyl]-4-isopropyl-4-methyl-1,3-oxazol-5-one 40 ml of glacial acetic acid, 1.96 g (0.019 mole) of concentrated sulfuric acid and 0.36 g (0.02 mole) of water were added to 5.56 g (0.02 mole) of 2-(4-chlorophenyl)-N-(1-cyano-1,2-dimethylpropyl)propanamide. The mixture was stirred at 60° C. for 2 hours to give rise to a reaction. After the completion of the reaction, the reaction mixture was cooled. Thereto were added 400 ml of water and 400 ml of ethyl acetate for layer separation. The organic layer was washed with a saturated aqueous sodium bicarbonate solution and a saturated aqueous sodium chloride solution, and concentrated to obtain 5.58 g of 2-[1-(4-chlorophenyl)ethyl]-4-isopropyl-4-methyl-1,3-oxazol-5-one (yield=100%).

EXAMPLE 3
(The Invention Described in the Above [2])

Production of 2-[1-(4-chlorophenyl)ethyl]-4-isopropyl-4-methyl-1,3-oxazol-5-one 450 ml of toluene, 45 g (0.44 mole) of concentrated sulfuric acid and 45 ml of glacial acetic acid were added to 126.7 g (0.45 mole) of 2-(4-chlorophenyl)-N-(1-cyano-1,2-dimethylpropyl)propanamide. The mixture was refluxed for 4 hours with heating, to give rise to a reaction. After the completion of the reaction, the reaction mixture was cooled and dropwise added to a solution of 18.2 g (0.45 moles) of sodium hydroxide dissolved in 300 ml of water. The organic layer was separated, then washed with a saturated aqueous sodium bicarbonate solution and water, and concentrated to obtain 125 g (0.448 mole) of 2-[1-(4-chlorophenyl)ethyl]-4-isopropyl-4-methyl-1,3-oxazol-5-one (yield=99.6%).

EXAMPLE 4
(The Invention Described in the Above [3])

Production of ethyl 4-[2-(4-chlorophenyl)propanoylamino]-4,5-dimethyl-3-oxohexanoate 0.73 g (0.00722 mole) of triethylamine and 0.41 g (0.0043 mole) of magnesium chloride were added, at room temperature, to a solution of 0.73 g (0.0043 mole) of monopotassium ethyl malonate dissolved in :10 ml of acetonitrile, followed by stirring. Thereto was added 0.8 g (0.00287 mole) of 2-[1-(4-chlorophenyl)ethyl]-4-isopropyl-4-methyl-1,3-oxazol-5-one. The mixture was stirred at 60° C. for 5 hours to give rise to a reaction. After the completion of the reaction, the reaction mixture was cooled. Thereto were added 50 ml of water and diluted hydrochloric acid to adjust the mixture to a pH of 4 or less. The mixture was subjected to extraction with ethyl acetate. The organic layer was washed with a saturated aqueous sodium bicarbonate solution and a saturated aqueous sodium chloride solution, then dried over anhydrous sodium sulfate, and concentrated. The concentrate was subjected to separation by column chromatography to obtain 0.5 g (0.00136 mole) of ethyl 4-[2-(4-chlorophenyl)propanoylamino]-4,5-dimethyl-3-oxohexanoate (yield=48%).

EXAMPLE 5
(The Invention Described in the Above [3])

Production of ethyl 4,5-dimethyl-3-oxo-4-(benzoylamino)hexanoate 1.06 g (0.01 mole) of triethylamine and 0.85 g (0.01 mole) of magnesium chloride were added, at room temperature, to a solution of 0.85 g (0.005 mole) of monopotassium ethyl malonate dissolved in 10 ml of acetonitrile, followed by stirring. Thereto was added 1.1 g (0.005 mole) of 2-phenyl-4-isopropyl-4-methyl-1,3-oxazol-5-one. The mixture was stirred at 60° C. for 8 hours to give rise to a reaction. After the completion of the reaction, the reaction mixture was cooled. Thereto were added 50 ml of water and diluted hydrochloric acid to adjust the mixture to a pH of 4 or less. The mixture was subjected to extraction with ethyl acetate. The organic layer was washed with a saturated aqueous sodium bicarbonate solution and a saturated aqueous sodium chloride solution, then dried over anhydrous sodium sulfate, and concentrated. The concentrate was subjected to separation by column chromatography to obtain 0.4 g (0.00131 mole) of ethyl 4,5-dimethyl-3-oxo-4-(benzoylamino)hexanoate (yield=26%).

EXAMPLE 6
(The Invention Described in the Above [3])

Production of ethyl 4-(acetylamino)-4,5-dimethyl-3-oxo-hexanoate 0.91 g (0.01 mole) of triethylamine and 0.43 g (0.0045 mole) of magnesium chloride were added, at room temperature, to a solution of 0.76 g (0.0045 mole) of monopotassium ethyl malonate dissolved in 10 ml of acetonitrile, followed by stirring. Thereto was added 0.47 g (0.003 mole) of 2-methyl-4-isoporpyl-4-methyl-1,3-oxazol-5-one. The mixture was stirred at 65° C. for 10 hours to give rise to a reaction. After the completion of the reaction, the reaction mixture was cooled. Thereto were added 50 ml of water and diluted hydrochloric acid to adjust the mixture to a pH of 4 or less. The mixture was subjected to extraction with ethyl acetate. The organic layer was washed with a saturated aqueous sodium bicarbonate solution and a saturated aqueous sodium chloride solution, then dried over anhydrous sodium sulfate, and concentrated. The concentrate was subjected to separation by column chromatography to obtain 0.2 g (0.00081 mole) of ethyl 4-(acetylamino)-4,5-dimethyl-3-oxohexanoate (yield=27%).

EXAMPLE 7
(The Invention Described in the Above [3])

Production of methyl 4-[2-(4-chlorophenyl) propanoylamino]-4,5-dimethyl-3-oxohexanonate In a reactor were placed 4.6 g (0.029 mole) of monopotassium methyl malonate, 7.5 ml of toluene and 10 ml of dimethylformamide. The mixture was cooled to 10° C. Thereto were added 3.0 g (0.032 mole) of magnesium chloride and 2.1 g (0.021 mole) of triethylamine, followed by stirring. Thereto was dropwise added a solution of 5.6 g (0.020 mole) of 2-[1-(4-chlorophenyl)ethyl]-4-isopropyl-4-methyl-1,3-oxazl-5-one dissolved in 2.5 ml of toluene. The mixture was stirred at 80° C. for 20 hours to give rise to a reaction. After the completion of the reaction, the reaction mixture was cooled. Thereto were added 20 ml of water and 4.4 g of sulfuric acid, followed by stirring at 50° C. for 1 hour. Thereto was added 30 ml of toluene, and layer separation was conducted at 50° C. The toluene layer was washed with a saturated aqueous sodium bicarbonate solution and a saturated aqueous sodium chloride solution, and concentrated. The resulting crude crystals were recrystallized from n-hexane to obtain 1.2 g (0.0034 mole) of methyl 4-[2-(4-chlorophenyl)propanoylamino]-4,5-dimethyl-3-oxohexanonate (yield=17%).

EXAMPLE 8
(The Invention Described in the Above [3])

Production of ethyl 4-[2-(4-chlorophenyl) propanoylamino]-4,5-dimethyl-3-oxohexanonate In a reactor were placed 51.0 g (0.3 mole) of monopotassium ethyl malonate, 100 ml of toluene and 100 ml of dimethylformamide. The mixture was cooled to 10° C. Thereto were added 20.9 g (0.22 mole) of magnesium chloride and 22.2 g (0.22 mole) of triethylamine, followed by stirring. Thereto was added 56.0 g (0.2 mole) of 2-[1-(4-chlorophenyl)ethyl]-4-isopropyl-4-methyl-1,3-oxazol-5-one. The mixture was stirred at 80° C. for 12 hours to give rise to a reaction. After the completion of the reaction, the reaction mixture was cooled. Thereto were added 200 ml of water and 44 g of sulfuric acid, followed by stirring at 50° C. for 1 hour. Extraction was conducted with 300 ml of toluene. The toluene layer was washed with a saturated aqueous sodium bicarbonate solution and a saturated aqueous sodium chloride solution, and concentrated to obtain 62.5 g (0.17 mole) of ethyl 4-[2-(4-chlorophenyl) propanoylamino]-4,5-dimethyl-3-oxohexanonate (yield=85%).

EXAMPLE 9
(The Invention Described in the Above [3])

Production of isopropyl 4-[2-(4-chlorophenyl) propanoylamino]-4,5-dimethyl-3-oxohexanonate In a reactor were placed 5.52 g (0.03 mole) of monopotassium isopropyl malonate, 15 ml of toluene and 12 ml of dimethylformamide. The mixture was cooled to 10° C. Thereto were added 2.1 g (0.022 mole) of magnesium chloride and 2.2 g (0.022 mole) of triethylamine, followed by stirring. Thereto was added 5.6g (0.02 mole) of 2-[1-(4-chlorophenyl)ethyl]-4-isopropyl-4-methyl-1,3-oxazol-5-one. The mixture was stirred at 80° C. for 20 hours to give rise to a reaction. After the completion of the reaction, the reaction mixture was cooled. Thereto were added 20 ml of water and 4 g of sulfuric acid, followed by stirring at 50° C. for 1 hour. Extraction was conducted with 30 ml of toluene. The toluene layer was washed with a saturated aqueous sodium bicarbonate solution and a saturated aqueous sodium chloride solution, and concentrated to obtain 3.8 g (0.01 mole) of isopropyl 4-[2-(4-chlorophenyl)propanoylamino]-4,5-dimethyl-3-oxohexanonate (yield 50%, melting point= 110.4 to 112.8° C.).

EXAMPLE 10
(The Invention Described in the Above [3])

Production of ethyl 4-[(4-chlorophenyl) acetylamino]-5-methyl-3-oxohexanonate

In a reactor were placed 5.11 g (0.03 mole) of monopotassium ethyl malonate, 20 ml of toluene and 15 ml of dimethylformamide. The mixture was cooled to 10° C. Thereto were added 2.1 g (0.022 mole) of magnesium chloride and 2.22 g (0.022 mole) of triethylamine, followed by stirring. Thereto was added 5.3g (0.02 mole) of (4-chlorobenzyl)-4-isopropyl-4-methyl-1,3-oxazol-5-one. The mixture was stirred at 80° C. for 5 hours to give rise to a reaction. After the completion of the reaction, the reaction mixture was cooled. Thereto were added 40 ml of water and 4 g of sulfuric acid, followed by stirring at 50° C. for 1 hour. Extraction was conducted with 100 ml of toluene. The toluene layer was washed with a saturated aqueous sodium bicarbonate solution and a saturated aqueous sodium chloride solution, and concentrated to obtain 5.0 g (0.014 mole) of ethyl 4-[(4-chlorophenyl)acetylamino]-4,5-dimethyl-3-oxohexanonate (yield=70%).

EXAMPLE 11
(The Invention Described in the Above [4])

Production of 3-amino-3,4-dimethylpentan-2-one 10 ml of 10% hydrochloric acid was added to 0.5 g (0.00205 mole) of ethyl 4-(acetylamino)-4,5-dimethyl-3-oxohexanonate. The mixture was refluxed for 1 hour with heating. The reaction mixture was analyzed by gas chromatography to confirm formation of N-acetyl-1-isopropyl-1-methyl-2-oxopropanamide. To the reaction mixture was added 10 ml of concentrated hydrochloric acid, followed by refluxing for 6 hours with heating, to give rise to a reaction. After the completion of the reaction, the reaction mixture was washed with toluene to remove the neutral components. The aqueous layer was adjusted to a pH of 12 or more using an aqueous sodium hydroxide solution, and subjected to extraction with ethyl acetate. The organic layer was concentrated to obtain 0.2 g (0.00155 mole) of 3-amino-3,4-dimethylpentan-2-one (yield=76%).

EXAMPLE 12

(The Invention Described in the Above [4])

Production of 2-(4-chlorophenyl)-N-[1-methyl-1-(methylethyl)-2-oxopropyl]propanamide 10 ml of 3 N hydrochloric acid was added to 0.2 g (0.000544 mole) of ethyl 4-[2-(chlorophenyl) propanoylamino]-4,5-dimethyl-3-oxohexanonate. The mixture was refluxed for 3 hours with heating. The reaction mixture was analyzed by gas chromatography to confirm formation of 2-(4-chlorophenyl)-N-[1-methyl-1-(methylethyl)-2-oxopropyl]propanamide (conversion=100%).

EXAMPLE 13

(The Invention Described in the Above [4])

Production of 2-(4-chlorophenyl)-N-[1-methyl-1-(methylethyl)-2-oxopropyl]propanamide In a reactor were placed 57.5 g (0.156 mole) of 4-[2-(4-chlorophenyl)propanoylamino]-4,5-dimethyl-3-oxohexanoate, 156 ml of 2-propanol, 62.4 ml of water and 15.6 ml of concentrated sulfuric acid. The mixture was refluxed for 7 hours with heating, to give rise to a reaction. After the completion of the reaction, the reaction mixture was cooled to 60° C. 446 ml of water was added for further cooling. The mixture was neutralized with a 23% aqueous sodium hydroxide solution. The precipitated crystals were collected by filtration to obtain 41.5 g (0.14 mole) of 2-(4-chlorophenyl)-N-[1-methyl-1-(methylethyl)-2-oxopropyl]propanamide (yield=90%).

EXAMPLE 14

(The Invention Described in the Above [4])

Production of N-[1-methyl-1-(methylethyl)-2-oxopropyl]-(4-chlorophenyl)acetamide In a reactor were placed 2.5 g (0.007 mole) of 4-[(4-chlorophenyl)acetylamino]-4,5-dimethyl-3-oxohexanoate, 7 ml of 2-propanol, 8 ml of water and 0.7 ml of concentrated sulfuric acid. The mixture was refluxed for 5 hours with heating, to give rise to a reaction. After the completion of the reaction, the reaction mixture was cooled at room temperature. 20 ml of water was added. The mixture was neutralized with a 23% aqueous sodium hydroxide solution. The precipitated crystals were collected by filtration to obtain 2.37 g (0.0067 mole) of N-[1-methyl-1-(methylethyl)-2-oxopropyl]-(4-chlorophenyl)acetamide (yield=96.3%).

Industrial Applicability

According to the present invention, there are provided an amide compound which is a useful intermediate in production of a phenylalkanoic acid amide useful as a fungicide; a process for producing the amide compound; a process for producing an oxazolinone compound which is a raw material in production of the amide compound; and a process for producing a ketone compound which is also a useful intermediate in production of a phenylalkanoic acid amide, from the above amide compound.

What is claimed is:

1. A process for producing an amide compound represented by the following formula

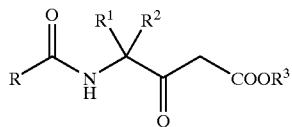

wherein R is an alkyl group, a cycloalkyl group, a haloalkyl group, an aryl group, a substituted aryl group, an arylalkyl group, a substituted arylalkyl group, an (aryl)(alkoxy)alkyl group or a (substituted aryl)(alkoxy)alkyl group; $R^1$ and $R^2$ are each independently an alkyl group, a cycloalkyl group, a haloalkyl group, an arylalkyl group, a substituted arylalkyl group, an aryl group, a substituted aryl group or a hydrogen atom, and may bond with each other to form a ring together with the carbon atom with which they bond; and $R^3$ is an alkyl group, a cycloalkyl group, a haloalkyl group, an arylalkyl group, a substituted arylalkyl group, an aryl group, a substituted aryl group or a hydrogen atom, which process comprises reacting a nitrile compound represented by the following formula

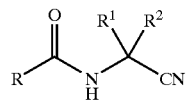

(wherein R, $R^1$ and $R^2$ each have the same definition as given above) with an acid to give rise to intramolecular ring closure to obtain an oxazolinone compound represented by the following general formula

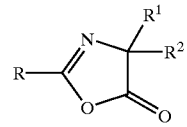

(wherein R, $R^1$ and $R^2$ each have the same definition as given above), and reacting the oxazolinone compound with a carboxy compound represented by the following general formula

(wherein Y is a hydrogen atom, a carboxyl group or a salt of the carboxyl group; and $R^3$ has the same definition as given above) in the presence of a base.

2. A process for producing an oxazolinone compound represented by the following general formula

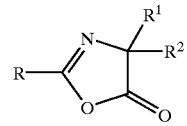

wherein R is an alkyl group, a cycloalkyl group, a haloalkyl group, an aryl group, a substituted aryl group, an arylalkyl group, a substituted arylalkyl group, an (aryl)(alkoxy)alkyl group or a (substituted aryl)

(alkoxy)alkyl group; and $R^1$ and $R^2$ are each independently an alkyl group, a cycloalkyl group, a haloalkyl group, an arylalkyl group, a substituted arylalkyl group, an aryl group, or a substituted aryl group, and may bond with each other to form a ring together with the carbon atom with which they bond, which process comprises reacting a nitrile compound represented by the following general formula

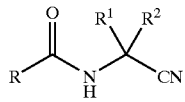

(wherein R, $R^1$ and $R^2$ each have the same definition as given above) with an acid to give rise to intramolecular ring closure.

3. A process for producing a amide compound represented by the following formula

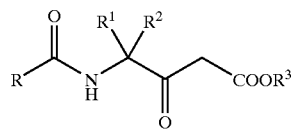

wherein R is an alkyl group, a cycloalkyl group, a haloalkyl group, an aryl group, a substituted aryl group, an arylalkyl group, a substituted arylalkyl group, an (aryl)(alkoxy)alkyl group or a (substituted aryl)(alkoxy)alkyl group; $R^1$ and $R^2$ are each independently an alkyl group, a cycloalkyl group, a haloalkyl group, an arylalkyl group, a substituted arylalkyl group, an aryl group, a substituted aryl group or a hydrogen atom, and may bond with each other to form a ring together with the carbon atom with which they bond; and $R^3$ is an alkyl group, a cycloalkyl group, a haloalkyl group, an arylalkyl group, a substituted arylalkyl group, an aryl group, a substituted aryl group or a hydrogen atom, which process comprises reacting an oxazolinone compound represented by the following formula

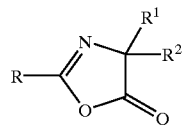

(wherein R, $R^1$ and $R^2$ each have the same definition as given above) with a carboxy compound represented by the following formula

(wherein Y is a hydrogen atom, a carboxyl group or a salt of the carboxyl group; and $R^3$ has the same definition as give above) in the presence of a base.

4. A process for producing a ketone compound represented by the following general formula

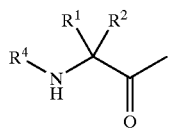

wherein $R^1$ and $R^2$ are each independently an alkyl group, a cycloalkyl group, a haloalkyl group, an arylalkyl group, a substituted arylalkyl group, an aryl group, a substituted aryl group or a hydrogen atom, and may bond with each other to form a ring together with the carbon atom with which they bond; and $R^4$ is an alkylcarbonyl group, a cycloalkylcarbonyl group, a haloalkylcarbonyl group, an arylcarbonyl group, a substituted arylcarbonyl group, an arylalkylcarbonyl group, a substituted arylalkylcarbonyl group, an (aryl)(alkoxy)alkylcarbonyl group, a (substituted aryl)(alkoxy)alkylcarbonyl group or a hydrogen atom, which process comprises reacting an amide compound represented by the following formula

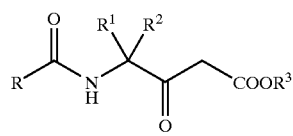

wherein R is an alkyl group, a cycloalkyl group, a haloalkyl group, an aryl group, a substituted aryl group, an arylalkyl group, a substituted arylalkyl group, an (aryl)(alkoxy)alkyl group or a (substituted aryl)(alkoxy)alkyl group; $R^1$ and $R^2$ each have the same definition as given above; and $R^3$ is an alkyl group, a cycloalkyl group, a haloalkyl group, an arylalkyl group, a substituted arylalkyl group, an aryl group, a substituted aryl group or a hydrogen atom with an acid or a base in the presence of water.

5. A process for producing an amide compound according to claim 1, wherein the base is selected from alkali metal bases, alkaline earth metal bases, organic amines and pyridines.

6. An acid amide compound represented by the following general formula

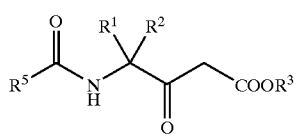

wherein $R^1$ is an alkyl group, a cycloalkyl group, a haloalkyl group, an arylalkyl group, a substituted arylalkyl group, an (aryl)(alkoxy)alkyl group or a (substituted aryl)(alkoxy)alkyl group; $R^1$ and $R^2$ are each independently an alkyl group, a cycloalkyl group, a haloalkyl group, an arylalkyl group, a substituted arylalkyl group, an aryl group, or a substituted aryl group, and may bond with each other to form a ring together with the carbon atom with which they bond; and $R^3$ is an alkyl group, a cycloalkyl group, a haloalkyl group, an arylalkyl group, a substituted arylalkyl group, an aryl group, a substituted aryl group or a hydrogen atom.

7. A process for producing an amide compound according to claim 3, wherein the base is selected from alkali metal bases, alkaline earth metal bases, organic amines and pyridines.

* * * * *